United States Patent
Föjer et al.

(10) Patent No.: US 11,339,454 B2
(45) Date of Patent: May 24, 2022

(54) METHOD FOR MANUFACTURING A HIGH STRENGTH STEEL SHEET AND SHEET OBTAINED

(71) Applicant: ArcelorMittal, Luxembourg (LU)

(72) Inventors: Gunhild Cécilia Föjer, Destelbergen (BE); Jan Mahieu, Dendermonde (BE)

(73) Assignee: ARCELORMITTAL, Luxembourg (LU)

(*) Notice: Subject to any disclaimer, the term of this patent is extended or adjusted under 35 U.S.C. 154(b) by 0 days.

(21) Appl. No.: 16/898,395

(22) Filed: Jun. 10, 2020

(65) Prior Publication Data

US 2020/0316807 A1 Oct. 8, 2020

Related U.S. Application Data

(63) Continuation of application No. 15/322,909, filed as application No. PCT/IB2015/055043 on Jul. 3, 2015.

(30) Foreign Application Priority Data

Jul. 3, 2014 (WO) .................. PCT/IB2014/002290

(51) Int. Cl.
| | |
|---|---|
| *C21D 9/46* | (2006.01) |
| *C22C 38/28* | (2006.01) |
| *C21D 8/02* | (2006.01) |
| *C22C 38/02* | (2006.01) |
| *C22C 38/00* | (2006.01) |
| *C22C 38/38* | (2006.01) |
| *C22C 38/06* | (2006.01) |
| *C22C 38/04* | (2006.01) |
| *A61F 13/02* | (2006.01) |
| *A61K 9/70* | (2006.01) |
| *B26D 7/18* | (2006.01) |
| *B26F 1/38* | (2006.01) |

(52) U.S. Cl.
CPC ............ *C21D 9/46* (2013.01); *A61F 13/0276* (2013.01); *A61K 9/7023* (2013.01); *B26D 7/18* (2013.01); *B26D 7/1818* (2013.01); *B26F 1/38* (2013.01); *C21D 8/0226* (2013.01); *C21D 8/0236* (2013.01); *C21D 8/0263* (2013.01); *C21D 8/0273* (2013.01); *C22C 38/001* (2013.01); *C22C 38/002* (2013.01); *C22C 38/02* (2013.01); *C22C 38/04* (2013.01); *C22C 38/06* (2013.01); *C22C 38/28* (2013.01); *C22C 38/38* (2013.01); *A61F 2013/0296* (2013.01); *C21D 8/02* (2013.01); *C21D 2211/001* (2013.01); *C21D 2211/002* (2013.01); *C21D 2211/005* (2013.01); *C21D 2211/008* (2013.01)

(58) Field of Classification Search
None
See application file for complete search history.

(56) References Cited

U.S. PATENT DOCUMENTS

| | | |
|---|---|---|
| 5,380,378 A | 1/1995 | Hemsath |
| 9,011,614 B2 | 4/2015 | Nakagaito et al. |
| 9,290,834 B2 | 3/2016 | Hasegawa |
| 9,567,659 B2 | 2/2017 | Somani et al. |
| 9,650,708 B2 | 5/2017 | Becker et al. |
| 10,174,396 B2 | 1/2019 | Takashima et al. |
| 2010/0139816 A1 | 6/2010 | Hanlon et al. |
| 2011/0146852 A1 | 6/2011 | Matsuda |
| 2013/0295402 A1 | 11/2013 | Oh et al. |
| 2014/0170439 A1 | 6/2014 | Allain et al. |

(Continued)

FOREIGN PATENT DOCUMENTS

| | | |
|---|---|---|
| EP | 2881481 A1 | 6/2015 |
| JP | 2005336526 A | 12/2005 |
| JP | 4324225 B1 | 9/2009 |
| JP | 2010-126770 A | 6/2010 |
| JP | 2014009376 A | 1/2014 |
| JP | 2014034716 A | 2/2014 |
| RU | 2437945 C2 | 12/2011 |
| RU | 2464338 C2 | 10/2012 |
| RU | 2491357 C1 | 8/2013 |
| WO | WO2012120020 A1 | 9/2012 |

(Continued)

OTHER PUBLICATIONS

Machine English translation of JP2010-126770, Kaneko Shinjiro et al., Jun. 10, 2010.

(Continued)

*Primary Examiner* — Anthony M Liang
(74) *Attorney, Agent, or Firm* — Davidson, Davidson & Kappel, LLC

(57) ABSTRACT

A method for manufacturing a steel sheet having a yield strength YS of more than 1000 MPa, a tensile strength TS of more than 1150 MPa and a total elongation E of more than 8%, includes the steps of—preparing a steel sheet through rolling from a steel containing in percent by weight 0.19% to 0.22% C, 2% to 2.6% Mn, 1.45% to 1.55% Si, 0.15% to 0.4% Cr, less than 0.020% P, less than 0.05% S, less than 0.08% N, 0.015% to 0.070% Al, the reminder being Fe and unavoidable impurities; and soaking the sheet at an annealing temperature TA between 860° C. and 890° C. for a time between 100 s and 210 s, cooling the sheet to a quenching temperature QT between 220° C. and 330° C., from a temperature TC not less than 500° C. at a cooling speed not less than 15° C./s, heating the steel sheet during a time between 115 s and 240 s up to a first overaging temperature TOA1 higher than 380° C., then heating the sheet during a time between 300 s and 610 s up to a second overaging temperature TOA2 between 420° and 450° C., cooling the steel sheet to a temperature less than 100° C. at a cooling speed less than 5° C./s. The structure of the steel contains more than 80% of tempered martensite, more than 5% of retained austenite, less than 5% of ferrite, less than 5% of bainite and less than 6% of fresh martensite.

3 Claims, No Drawings

(56) References Cited

U.S. PATENT DOCUMENTS

2016/0168656 A1 6/2016 Kawabe et al.
2016/0355900 A1 12/2016 Gil Otin et al.

FOREIGN PATENT DOCUMENTS

WO  WO2012153016 A1  11/2012
WO  WO2014061270 A1  4/2014

OTHER PUBLICATIONS

Wang et al., "Quenching and Partitioning Steel Heat Treatment," Metallography, Microstructure, and Analysis, Source info: vol. 2, No. 4, pp. 268-281 (2013).
Seo et al., "Application of Quenching and Partitioning (Q&P) Processing to Press Hardening Steel," Metallurgical and Materials Transactions A, Springer US, New York, vol. 45, No. 9, pp. 4022-4037 (2014).
Andrews, "Empirical formulae for the calculation of some transformation temperatures," Journal of The Iron and Steel Institute, pp. 721-727 (1965).

METHOD FOR MANUFACTURING A HIGH STRENGTH STEEL SHEET AND SHEET OBTAINED

This is a continuation of U.S. application Ser. No. 15/322,909 which has a filing date of Dec. 29, 2016 and which is a national stage of PCT/IB2015/055043 filed Jul. 3, 2015 which claims priority to PCTIB2014/002290 filed Jul. 3, 2014, the entire disclosures of which are hereby incorporated by reference herein.

The present invention relates to high strength steel sheets excellent in workability and yield strength and to a method for producing the same.

BACKGROUND

To manufacture various equipments such as trailers, trolleys, buses, trucks, agricultural machines, garbage trucks, automotive parts, and so on, high strength steel sheets made of DP (dual phase) steels or TRIP (transformation induced plasticity) steels are usually used. Some of such steels, for example TRIP steels having a martensitic structure with some retained austenite and containing about 0.2% C, about 2% Mn, about 1.7% Si, have a tensile strength TS of about 980 MPa, a yield strength YS of about 750 MPa and an elongation E of more than 8%. These sheets are produced on continuous annealing lines comprising an overaging section in which the sheets remain a few hundreds of seconds.

In order to reduce the weight of the equipments made of these steels, it is very desirable to increase the tensile strength and the yield strength without decreasing the elongation which is necessary to have a good workability and without reducing the weldability. But, with DP or TRIP steels, even if it is possible to obtain a tensile strength of more than 1500 MPa, when the elongation is of more than 8% the yield strength remains inferior to 950 MPa and when the yield strength is higher than 1000 MPa, the elongation does not reach 8%.

By increasing the Mn content of such steels to more than 2.6% and adding some microalloying elements such as Ti, it is possible to obtain sheets having a yield strength higher than 1000 MPa, a tensile strength higher than 1150 MPa and an elongation of more than 8%. But the need to increase the Mn content has the disadvantage of increasing significantly the segregation phenomena, and the need to add elements such as Ti has the disadvantage of reducing the total elongation due to small precipitates.

It also seems possible to obtain such characteristics by adding about 0.25% of Mo. But with such addition the sheets are not cold rollable in good conditions. Therefore, due to the limitations of hot rolling, it is not possible to produce sheets having the needed thickness.

SUMMARY

So, it remains desirable to be able to produce a cold rolled steel sheet having a yield strength of more than 1000 MPa, a tensile strength of more than 1150 MPa and an elongation of more than 8%, using a continuous annealing line comprising an overaging section in which the sheet remains a few hundreds of seconds, without adding too much Mn and/or microalloying elements.

For this purpose, a method is provided for manufacturing a steel sheet having a yield strength YS of more than 1000 MPa, a tensile strength TS of more than 1150 MPa and a total elongation E of more than 8%, the method comprising the steps of:

preparing a steel sheet through rolling from a steel containing in percent by weight 0.19% to 0.22% C, 2% to 2.6% Mn, 1.45% to 1.55% Si, 0.15% to 0.4% Cr, less than 0.020% P, less than 0.011% S, less than 0.008% N, 0.015% to 0.070% Al, the reminder being Fe and unavoidable impurities, annealing the rolled steel sheet, the annealing comprising a step of soaking the sheet at an annealing temperature TA between 860° C. and 890° C. for a time between 100 s and 210 s, cooling the annealed sheet to a quenching temperature TQ between 220° C. and 330° C., the cooling comprising a step of cooling the sheet from an initial cooling temperature TC not less than 500° C. to the quenching temperature TQ at a cooling speed not less than 15° C./s, heating the steel sheet during a time between 115 s and 240 s up to a first overaging temperature TOA1 higher than 380° C., then heating the sheet during a time between 300 s and 610 s up to a second overaging temperature TOA2 between 420° and 450° C. and, cooling the steel sheet to a temperature less than 100° C. at a cooling speed less than 5° C./s.

the steel sheet having a structure containing more than 80% of tempered martensite, more than 5% of retained austenite, less than 5% of ferrite, less than 5% of bainite and less than 6% of fresh martensite.

The annealing can comprise a second step of soaking the sheet at a temperature between the annealing temperature TA and 795° C. for a time between 90 s and 190 s;

The method can further comprise between the second step of soaking and the step of cooling, a step of initial cooling at a cooling speed between 7° C./s and 16° C./s from the temperature at the end of the second step of soaking to the initial cooling temperature TC.

The preparation of the steel sheet through rolling can comprise the steps of:

heating a slab made of the steel corresponding to the invention, at a temperature higher than 1030° C., hot rolling the slab to obtain a hot rolled sheet having a thickness between 2 mm and 3 mm, with a end of rolling temperature higher than 880° C., preferably between 890° C. and 910° C., coiling the hot rolled sheet at a temperature between 520° C. and 600° C., preferably between 550° C. and 570° C., cold rolling the hot rolled sheet with a reduction between 50% and 60% in order to obtain a cold rolled sheet having a thickness between 0.7 mm and 1.5 mm.

The method can further comprise between the step of coiling and the step of cold rolling, a step of batch annealing at a temperature between 600° C. and 700° C. for more than 30 hours under an HNX atmosphere.

A high-strength steel-sheet is also provided having a yield strength YS of more than 1000 MPa, a tensile strength TS of more than 1150 MPa and a total elongation E of more than 8%, made of steel containing, on a weight basis, 0.19% to 0.22% C, 2% to 2.6% Mn, 1.45% to 1.55% Si, 0.15% to 0.4% Cr, less than 0.020% P, less than 0.0011% S, less than 0.008% N, 0.015% to 0.07% Al, the reminder being Fe and unavoidable impurities, the steel having a microstructure containing more than 80% of tempered martensite, more than 5% of retained austenite, less than 5% of ferrite, less than 5% of bainite and less than 6% of fresh martensite.

Preferably, the amount of carbon in the retained austenite is of at least 0.9%, and preferably of at most 1.5%.

Still preferably, the amount of carbon in the retained austenite is comprised between 0.9% and 1.2%.

DETAILED DESCRIPTION

The invention will now be described in detail and illustrated by examples without introducing limitations.

The composition of the steel according to embodiments of the invention comprises in % in weight:

- 0.19%≤C≤0.22% for ensuring a satisfactory strength and improving the stability of the retained austenite which is necessary to obtain a sufficient elongation. If carbon content is too high, the hot rolled sheet is hard to cold roll and the weldability is insufficient.
- 2%≤Mn≤2.6%. Manganese content has to be of more than 2% and preferably of more than 2.1% to have a sufficient hardenability in order to be able to obtain a structure comprising at least 80% of tempered martensite considering the cooling capacity of the continuous annealing line on which the sheet will be manufactured and because below 2% the tensile strength will be below 1150 MPa. Above 2.6%, segregation issues will appear which is detrimental to formability. In a preferred embodiment, Mn content is below or equal to 2.3% to reduce segregation issues.
- 1.3%≤Si≤1.6%; preferably Si≥1.45%; preferably Si≤1.55%. Si content has to be sufficient in order to stabilize the austenite and to provide solid solution strengthening. Moreover, Si retards the formation of carbides during carbon redistribution from martensite to austenite resulting from the overaging, thus keeping carbon in solution to stabilize the austenite. But at too high Si content, silicon oxides will form at the surface and this is detrimental to coatability.
- 0.15%≤Cr≤0.4% to increase the hardenability and to stabilize the retained austenite in order to delay the formation of bainite during overaging treatment. Preferably the chromium content is higher or equal to 0.30%.
- P≤0.02%. Phosphorus may reduce the carbides formation and thereby promote the redistribution of carbon to austenite. But too high P addition embrittles the sheet at hot rolling temperatures and reduces the toughness of the martensite.
- S≤0.011% and preferably ≤0.005%. Sulfur is an impurity which may embrittle the intermediate or final product.
- N≤0.008%. This element results from the elaboration. It can form aluminum nitrides which limit coarsening of austenite grain during annealing.
- 0.015%≤Al≤0.070%. Aluminum is usually added to liquid steel for the purpose of deoxidation. Moreover, the reminder of aluminum which is not combined with oxygen may form nitrides which limit the coarsening of austenite grain size at high temperature.

The reminder of the composition is iron and unavoidable impurities. In embodiments of the invention, Ni, Mo, Cu, Ti, Nb, V, B and so on are considered as impurities. Therefore, their contents are less than 0.050% for Ni, 0.04% for Mo, 0.01% for Cu, 0.007% for Ti, 0.005% for Nb, 0.007% for V, 0.0007% for B.

To manufacture a sheet according to embodiments of the invention, first of all, a semi-finished product such as a slab is hot rolled in order to obtain a hot rolled sheet. The hot rolled sheet is then cold rolled to obtain a cold rolled sheet having the desired thickness. Then, the cold rolled sheet is heat treated using a continuous annealing line in order to obtain the desired microstructure and the desired mechanical properties which are YS≥1000 MPa, TS≥1150 MPa and E (total elongation)≥8%.

For hot rolling, the slab heating temperature is higher than 1030° C. in order to have a complete dissolution of the carbides. In order to prevent the increase in scale loss, this temperature must remain under 1340° C. But, preferably it must remain less than 1150° C. in order not to have a too high finishing temperature.

The finishing temperature or temperature of end of rolling must be higher than 880° C. to remain higher than the $Ac_3$ transformation point of the steel in order to obtain an homogeneous structure without band-like microstructure. This temperature must remain less than 1000° C. in order not to be above the non-recrystallization temperature. Preferably the finishing temperature must remain in the range 890° C.-910° C., the optimum finishing temperature being 900° C.

After hot rolling, the hot rolled sheet which has a thickness generally comprised between 2 mm and 3 mm is coiled at a temperature between 520° C. and 600° C. and preferably between 550° C. and 570° C. The coiling temperature has to be higher than 520° C. to have a hot rolled sheet able to be cold rolled without the use of too high cold rolling forces and less than 570° C. in order to avoid inter-granular oxidation that is detrimental to fatigue properties.

Optionally, the sheet is batch annealed in order to homogenize the hardness and to reduce the brittleness of the edges and the extremities of the sheet. The batch annealing is made at a temperature between 600° C. and 700° C. under an HNX atmosphere. Preferably the annealing time is of more than 30 hours. Then the sheet is cooled slowly down to 70° C. Preferably, the cooling must need at least 30 hours.

Then, the sheet is cold rolled with a reduction ratio preferably between 50% and 60% in order to reach the desired thickness which is between 0.7 mm and 1.5 mm, preferably higher than 0.8 mm and/or less than 1.4 mm.

The cold rolled sheet is then annealed in a continuous annealing line with a minimum line speed of 50 m/min. It is the speed at which the sheet scrolls in the line. This speed depends on the thickness of the sheet. It is well known in the art that in such continuous line, the more the sheet is thick, the more the speed is slow.

The continuous line comprises at least a heating zone able to heat the sheet up to an annealing temperature, a soaking zone which can be divided in two parts, the first one which is a radiant tube furnace and the second one, which is able to maintain the sheet at the annealing temperature for a time of few hundreds of seconds, an initial cooling zone to cool the sheet at a not too high cooling speed down to a temperature of beginning of rapid cooling, a rapid cooling zone able to quench the sheet down to a quenching temperature TQ at which the rapid cooling is stopped, a first and a second part of an overaging zone able to heat and maintain the sheet at temperatures corresponding to an overaging step, and a final cooling zone able to cool the sheet down to the ambient temperature.

In the heating zone, the sheet is heated up to the annealing temperature which is higher than 860° C. to be higher than the $Ac_3$ transformation point of the steel, in order to obtain a completely austenitic structure, but preferably lower than 890° C. in order not to coarsen too much the austenitic grains.

In the first part of the soaking zone comprising radiant tubes, the sheet is maintained at the annealing temperature TA or about this temperature but above 860° C. for a time of 100 to 200 seconds depending on the speed of the sheet, this speed depending on the thickness of the sheet.

In the second part of the soaking zone the sheet is maintained at the annealing temperature for a time of about 80 seconds to about 180 seconds, depending on the thickness of the sheet. The temperature of the sheet slowly decreases such that at the end of the zone the temperature is less than the annealing temperature but remains higher than 795° C.

After the soaking, the sheet passes through a first cooling zone in which it is cooled down to a temperature TC not less than 500° C. at a cooling speed between 7° C./s and 16° C./s, depending on the thickness of the sheet. The more the sheet is thick, the more the cooling speed is slow.

After this first cooling, the structure of the sheet remains fully austenitic.

Then, the sheet passes through a zone of rapid cooling in which it is cooled at a speed not less than 15° C./s from the temperature TC of the end of the first cooling down to quenching temperature QT between 220° C. and 330° C. The cooling speed depends on the thickness of the sheet, but is always higher than the critical quenching rate in order to obtain a martensitic structure with retained austenite. This structure may additionally contain some ferrite, but less than 5%, preferably less than 2% and ideally no ferrite at all.

The quenching temperature is chosen in order to obtain a structure containing at least more than 5% of retained austenite and preferably about 15%. In order to obtain about 15% of retained austenite, the theoretical optimum quenching temperature for a steel having a composition according to embodiments of the present invention is about 235° C. Therefore, preferably, the quenching temperature is between 220° C. and 245° C.

After the quenching, the sheet passes through an overaging section able to heat the sheet up to a temperature between 350° C. and 450° C. In this overaging zone, the temperature is measured at two different points dividing this overaging zone in two zones, the first measurement being made a few meters after the entry of the overaging section and the second one being made at the exit of the overaging section.

In the first zone, the sheet is heated during a time between 115 s and 240 s depending on the thickness in order to be progressively heated up to a first overaging temperature TOA1 higher than 350° C. and preferably higher than 380° C.

In the second zone, the sheet is heated during a time between 300 s and 610 s depending on the thickness of the sheet in order to be heated from the first overaging temperature up to a second overaging temperature TOA2 higher than TOA1, TOA2 being between 420° C. and 450° C.

The purpose of this treatment is to transfer carbon from the martensite to the austenite in order to enrich the austenite in carbon so that when the sheet is cooled to a temperature less than 70° C., the austenite remains stable. The amount of carbon in the retained austenite is of at least 0.9%, which ensures a sufficient stabilization of the retained austenite, and up to 1.5%. Over 1.5% of carbon in the retained austenite, said retained austenite would be too hard. Preferably, the amount of carbon in the retained austenite is comprised between 0.9% and 1.2%.

Moreover the martensite is depleted in carbon without carbide formation which makes it less brittle.

The duration and the temperature of the overaging are such that there is few and preferably no formation of bainite.

After the overaging treatment, the sheet is cooled down to a temperature less than 70° C. at a cooling speed preferably less than 5° C./s in order to have no or few formation of fresh martensite. But this cooling speed must be sufficiently high to have no or few formation of bainite and to be compatible with the characteristics of the line and the speed of the sheet.

With such treatment, it is possible to obtain a sheet having the chemical composition as defined above, with a structure containing more than 80% of martensite, and preferably more than 85%, at least 5% preferably more than 8% of retained austenite, less than 5% and preferably less than 2% of ferrite.

The amount of carbon in the retained austenite after cooling down to room temperature remains of at least 0.9%, and up to 1.5%, preferably between 0.9% and 1.2%.

The martensite is preferably tempered without carbides i.e. martensite with reduced carbon content resulting from the overaging. But it can also contain up to 6% of fresh martensite and some bainite, the latter structure content being less than 5% and preferably less than 2%. In any case it is preferable than the structure contents at least 80% of tempered martensite.

The proportion of retained austenite is preferably measured by XRD method which is the method that gives the less underestimated results.

With such structure, the sheet has a yield strength YS higher than 1000 MPa, a tensile strength TS higher than 1150 MPa and a total elongation E of more than 8%.

In order to determine the chemical composition of the steel with which it is possible to obtain the desired results, some trials were made with samples S1, S2, S3 and S4 having the composition reported in table 1, in % by weight.

TABLE 1

| Sample | Type | C | Mn | Si | Cr | Ti | Cu | Ni | Mo | Al |
| --- | --- | --- | --- | --- | --- | --- | --- | --- | --- | --- |
| S1 | CMnSi | 0.2 | 1.63 | 1.63 | — | — | — | — | — | — |
| S2 | CMnSiMo | 0.188 | 2.0 | 1.6 | — | — | — | — | 0.28 | 0.055 |
| S3 | CMnSiCuNi | 0.18 | 1.7 | 0.79 | — | — | 1.3 | 0.5 | — | — |
| S4 | CMn Si Cr | 0.2 | 2.15 | 1.5 | 0.35 | — | — | — | — | — |

The chemical compositions were chosen in order to obtain a martensite structure with significant amount of retained austenite.

The steels were produced, hot rolled then cold rolled on an industrial scale and samples were heat treated using salt bath treatments.

The heat treatments consisted in an annealing at a temperature of annealing TA higher than $Ac_3$ a quenching down to a quenching temperature QT followed by an overaging at an overaging temperature TOA during an overaging time OA Time. The quenching temperature was chosen in order to obtain a martensitic structure with significant amount of retained austenite.

The conditions of heat treatment and the obtained results: yield strength YS, tensile strength TS, total elongation E, fraction of retained austenite % γ are reported in table 2:

TABLE 2

| Sample | TA °C. | QT °C. | TOA °C. | OA Times | YS MPa | TS MPa | E % | γ % |
|---|---|---|---|---|---|---|---|---|
| S1 | 850 | 235 | 300-450 | 490 | 437 | 826 | 24.3 | not measured |
| S2 | 850 | 240 | 400 | 300 | 1083 | 1283 | 13 | 13.6 |
| S3 | 850 | 200 | 400 | 300 | 983 | 1144 | 7.7 | 3 |
| S4 | 850 | 235 | 300-450 | 490 | 1011 | 1221 | 13.6 | 7 |

For samples S1 and S4 the overaging was not a holding at a constant temperature, but a holding at a temperature growing regularly from 300° C. at the beginning of the holding to 450° C. at the end of the holding.

All annealing temperatures were higher than the $AC_3$ temperatures of the steels; therefore, before quenching the structure was completely austenitic.

After quenching the structure was martensitic with some retained austenite for samples S2, S3 and S4.

For sample S1, the structure contained also a few fractions of ferrite and bainite.

These results show that the desired properties can be reached only with the steels of S2, i.e. CMnSiMo steel and of S4, i.e. CMnSiCr steel. But the production of sheets corresponding to these steels showed that CMnSiMo steel was too difficult to cold roll because, after hot rolling and coiling at a temperature between 530° C. and 550° C., the steel was too hard to be cold rolled.

Therefore these results show that the only acceptable type of steel useful to manufacture cold rolled sheets having the desired properties (YS>1000 MPa, TS>1150 MPa, E>8%) is the type CMnSiCr containing about 0.2% C, about 2.3% Mn, about 1.5% Si and 0.35% Cr.

With this steel, sheets were produced by hot rolling and cold rolling, then heat treated on a continuous annealing line.

Two casts were used, the compositions of which are reported in table 3:

TABLE 3

| | C (%) | Mn (%) | Si (%) | P ppm | S ppm | Al (%) | N ppm | Ti ppm | Cr (%) |
|---|---|---|---|---|---|---|---|---|---|
| Cast 1 | 0.196 | 2.18 | 1.50 | 116 | 40 | 0.041 | 46 | 36 | 0.36 |
| Cast 3 | 0.203 | 2.25 | 1.46 | 112 | 19 | 0.039 | 38 | 18 | 0.38 |

The steel was continuously cast to obtain slabs. The slabs were hot rolled to obtain hot coils (or hot rolled sheets) whose thicknesses were 2.8 mm and 2.05 mm.

The slabs were heated at 1050° C. and the rolling was finished at a temperature between 930° C. and 950° C. for Cast 1 and between 860° C. and 910° C. for Cast 3.

During the first cold rolling tests, edge cracks appeared due to a too high hardness of the edges of the hot rolled sheet.

Other sheets were batch annealed at 650° C. during 6 hours under an HNX atmosphere. After this batch annealing, there was no more cold rolling difficulties.

The hot rolled sheets were cold rolled to obtain cold rolled sheets having thicknesses of 0.8 mm, 1 mm and 1.4 mm.

The cold rolled sheets were heat treated on a continuous annealing line, the line speed being between 50 m/mn and 100 m/mn depending on the thickness of the sheet and on the desired quenching temperature.

On the continuous line, the heat treatment comprised the following steps:

heating the sheet from the ambient temperature to an annealing temperature TA;

soaking the sheet at the annealing temperature TA1 (first soaking);

soaking the sheet at a temperature TA2 between the annealing temperature and 795° C., the temperature of the sheet decreases regularly and slowly from the annealing temperature TA1 to the temperature TA2 (second soaking);

cooling the sheet down to an initial cooling temperature TC not less than 500° C. (initial cooling);

cooling the sheet from the temperature TC down to a quenching temperature TQ at a cooling speed higher than 15° C./s in order to quench the sheet;

heating the sheet during a time $t_1$ between 115 and 240 s up to a first overaging temperature TOA1;

heating the sheet during a time $t_2$ between 300 s and 610 s from the first overaging temperature to a second overaging temperature TOA2;

cooling the sheet down to the room temperature (or ambient temperature).

The parameters of the heat treatments and the mechanical properties that were obtained for examples and counter examples are reported in table 4.

In table 4 the examples C-1, C-2 and C-3 are counter examples and E-1, E-2, E-3, E-4, E-5, E-6 and E-7 are examples according to embodiments of the invention.

TABLE 4

| Examples | Cast No | Thickness mm | TA1 °C. | TA2 °C. | TC °C. | TQ °C. | Cooling rate °C./s | $t_1$ s | TOA1 °C. | $t_2$ s | TOA2 °C. | YS MPa | TS MPa | E % |
|---|---|---|---|---|---|---|---|---|---|---|---|---|---|---|
| C-1 | 1 | 1.4 | 851 | 813 | 540 | 235 | 23 | <u>149</u> | <u>340</u> | 380 | 443 | <u>903</u> | 1126 | 15.1 |
| E-1 | 1 | 0.8 | 880 | 822 | 652 | 227 | 50 | 119 | 420 | 304 | 450 | 1067 | 1211 | 13.2 |
| E-2 | 1 | 1.5 | 860 | 795 | 650 | 228 | 29 | 216 | 396 | 552 | 451 | 1047 | 1208 | 11.6 |
| E-3 | 3 | 1.4 | 870 | 836 | 650 | 220 | 24 | 238 | 407 | 608 | 450 | 1106 | 1261 | 12.1 |
| E-4 | 3 | 0.8 | 870 | 828 | 675 | 245 | 37 | 132 | 405 | 338 | 420 | 1135 | 1282 | 8.6 |
| C-2 | 3 | 0.8 | 870 | 812 | 635 | 235 | 40 | 132 | 395 | <u>338</u> | <u>404</u> | 1169 | 1365 | <u>6.8</u> |
| C-3 | 3 | 1.0 | 870 | 829 | 680 | 225 | 32 | <u>149</u> | <u>355</u> | 380 | <u>385</u> | 1176 | 1351 | <u>6.7</u> |

TABLE 4-continued

| Examples | Cast No | Thickness mm | TA1 °C. | TA2 °C. | TC °C. | TQ °C. | Cooling rate °C./s | $t_1$ s | TOA1 °C. | $t_2$ s | TOA2 °C. | YS MPa | TS MPa | E % |
|---|---|---|---|---|---|---|---|---|---|---|---|---|---|---|
| E-5 | 3 | 1.4 | 860 | 801 | 660 | 310 | 30 | 159 | 396 | 405 | 450 | 1015 | 1188 | 13.9 |
| E-6 | 3 | 1.0 | 860 | 797 | 650 | 290 | 40 | 132 | 400 | 338 | 450 | 1056 | 1215 | 13 |
| E-7 | 3 | 0.8 | 860 | 797 | 660 | 275 | 50 | 238 | 280 | 608 | 450 | 1115 | 1254 | 11.4 |

In this table, it can be seen that the first and second overaging temperatures do not depend only from the thickness and the duration of heating (i.e. the speed of the sheet in the line). This results from the fact that the heating power of each zone can be partially adjusted.

The counter example C-1 exhibits a low yield strength due to the presence of too much ferrite. This results from the fact that the annealing temperature TA1 is too low. This temperature 851° C. is less than the AC3 temperature. Thus, the steel is not completely austenitic before quenching and it remains more than 5% of ferrite.

The counter examples C-2 and C-3 exhibit a low elongation because the overaging temperatures are too low and the martensite was not sufficiently tempered. Moreover, the retained austenite was insufficiently enriched in carbon, so the austenite was not sufficiently stabilized and more than 6% fresh martensite was formed.

Examples E-5, E-6 and 5-7 show that the quenching temperature does not need to be as low as 235° C. which is calculated optimal temperature.

But the examples E-1 to E-7 show that it is possible to reach the desired mechanical properties.

What is claimed is:

1. A high-strength steel sheet having a yield strength YS of more than 1000 MPa, a tensile strength TS of more than 1150 MPa and a total elongation E of more than 8%, comprising:

a steel composition including, in percent by weight:
0.19% to 0.22% C;
2% to 2.6% Mn;
1.45% to 1.55% Si;
0.15% to 0.4% Cr;
less than 0.020% P;
less than 0.0011% S;
less than 0.008% N;
less than 0.007% Ti; and
0.015% to 0.07% Al;
a remainder being Fe and unavoidable impurities; and
a microstructure including, by volume, more than 80% of tempered martensite, more than 5% of retained austenite, less than 5% of ferrite, less than 5% of bainite and less than 6% of fresh martensite, the retained austenite having a C amount of at least 0.9% by weight.

2. The high-strength steel sheet according to claim 1, wherein the retained austenite has a C amount between 0.9% and 1.5% by weight.

3. The high-strength steel sheet according to claim 2, wherein the retained austenite has a C amount between 0.9% and 1.2% by weight.

* * * * *